(12) United States Patent
Gibbons et al.

(10) Patent No.: US 8,008,034 B2
(45) Date of Patent: Aug. 30, 2011

(54) REDUCING OPTICAL INTERFERENCE IN A FLUIDIC DEVICE

(75) Inventors: Ian Gibbons, Portolla Valley, CA (US); Michael O'Connell, San Jose, CA (US)

(73) Assignee: Theranos, Inc., Palo Alto, CA (US)

( * ) Notice: Subject to any disclaimer, the term of this patent is extended or adjusted under 35 U.S.C. 154(b) by 1163 days.

(21) Appl. No.: 11/685,615

(22) Filed: Mar. 13, 2007

(65) Prior Publication Data

US 2010/0291609 A1    Nov. 18, 2010

Related U.S. Application Data

(63) Continuation of application No. 11/549,558, filed on Oct. 13, 2006.

(51) Int. Cl.
    *G01N 33/53* (2006.01)
(52) U.S. Cl. ......... 435/7.91; 435/4; 435/7.72; 435/69.2; 435/288.5; 427/2.11; 436/518; 436/543
(58) Field of Classification Search ........................ None
    See application file for complete search history.

(56) References Cited

U.S. PATENT DOCUMENTS

| | | | |
|---|---|---|---|
| 4,582,791 A | 4/1986 | Khanna et al. | |
| 5,441,894 A | 8/1995 | Coleman et al. | |
| 5,618,726 A | 4/1997 | Paszczynski et al. | |
| 5,744,320 A | 4/1998 | Sherf et al. | |
| 5,958,339 A * | 9/1999 | Belly et al. ............... | 422/56 |
| 6,352,862 B1 | 3/2002 | Davis et al. | |
| 6,989,128 B2 | 1/2006 | Alajoki et al. | |
| 2001/0031869 A1 * | 10/2001 | Akhavan-Tafti et al. ..... | 546/104 |
| 2002/0019059 A1 * | 2/2002 | Chow et al. ................ | 436/514 |
| 2002/0090633 A1 | 7/2002 | Becker et al. | |
| 2002/0106786 A1 | 8/2002 | Carvalho et al. | |
| 2003/0064507 A1 | 4/2003 | Gallagher et al. | |
| 2003/0152927 A1 | 8/2003 | Jakobsen et al. | |
| 2004/0014096 A1 * | 1/2004 | Anderson et al. ............ | 435/6 |
| 2004/0241051 A1 | 12/2004 | Wyzgol et al. | |
| 2006/0264782 A1 | 11/2006 | Holmes et al. | |
| 2006/0264783 A1 | 11/2006 | Holmes et al. | |
| 2008/0090256 A1 | 4/2008 | Gibbons et al. | |

FOREIGN PATENT DOCUMENTS

| | | |
|---|---|---|
| WO | WO 2006/121510 A2 | 11/2006 |
| WO | WO 2007/111651 A2 | 10/2007 |
| WO | WO 2006/121510 A3 | 4/2009 |
| WO | WO 2007/111651 A3 | 5/2009 |

OTHER PUBLICATIONS

European search report dated May 25, 2010 for Application No. 7868405.7.
International search report date Sep. 9, 2008 for PCT Application No. US07/80917.
Sambrook, et al. Molecular Cloning: A Laboratory Manual. 3rd Edition. Cold Spring Harbor Laboratory Press. New York. 2001. (Cover pages and table of contents only).

* cited by examiner

*Primary Examiner* — N. C. Yang
(74) *Attorney, Agent, or Firm* — Wilson Sonsini Goodrich & Rosati

(57) ABSTRACT

This invention is in the field of medical devices. Specifically, the present invention provides portable medical devices that allow real-time detection of analytes from a biological fluid. The methods and devices are particularly useful for providing point-of-care testing for a variety of medical applications. In particular, the medical device reduces interference with an optical signal which is indicative of the presence of an analyte in a bodily sample.

19 Claims, 6 Drawing Sheets

REDUCING OPTICAL INTERFERENCE IN A FLUIDIC DEVICE

CROSS-REFERENCE

This application is a continuation application of Ser. No. 11/549,558, filed Oct. 13, 2006, which is incorporated herein by reference in its entirety and to which application we claim priority under 35 USC §120, which is related to the following co-pending patent application Ser. No. 11/389,409, filed Mar. 24, 2006, which is incorporated herein by reference in its entirety.

BACKGROUND OF THE INVENTION

The discovery of a vast number of disease biomarkers and the establishment of miniaturized fluidic systems have opened up new avenues to devise methods and systems for the prediction, diagnosis and monitoring of treatment of diseases in a point-of-care setting. Point-of-care testing is particularly desirable because it rapidly delivers results to patients and medical practitioners and enables faster consultation between patients and health care providers. Early diagnosis allows a practitioner to begin treatment sooner and thus avoiding unattended deterioration of a patient's condition. Frequent monitoring of appropriate parameters such as biomarker levels and concentrations of therapeutic agents enables recognition of the effectiveness of drug therapy or early awareness that the patient is being harmed by the therapy. Examples of point-of-care analyses include tests for glucose, prothrombin time, drugs of abuse, serum cholesterol, pregnancy, and ovulation.

Fluidic devices can utilize a number of different assays to detect an analyte of interest in a sample of bodily fluid from a subject. In ELISA assays (a preferred technique for clinical assays especially in a point-of care context, if assay reagents such as enzyme-antibody conjugates and enzyme substrates remain on-board the fluidic device after the assay is performed, reagents unbound to the assay capture surface or excess reagents, if collected in the same fluidic device, can react with one another and create a signal that can interfere with the signal of interest produced by the assay. This is especially the case in luminogenic assays in which the assay reagents generate light, in contrast to assays that measure, for example, absorbance or fluorescence. Many luminogenic assays use an enzyme to generate luminescence thus improving assay sensitivity by amplification of the measured species. Moreover, in assay systems that contain all assay components, including waste washes in a small housing the potential for glowing luminogenic waste materials is further enhanced. In such assay formats, the excess or unbound enzyme-labeled reagent may react with enzyme substrate, thus creating undesired interfering signals.

Some fluidic device features may mitigate the problem of an interfering signal to a certain degree. For example, the body of the fluidic device can be opaque, optically isolating the undesired glow, or the detection system can be configured to reject light which does not originate from reaction sites within the fluidic device. These mitigating features, however, may not sufficiently eliminate the interference as light can still travel through transparent elements of the fluidic device and interfere with the signal of interest. This is especially the case in assays requiring high sensitivity where the ratio between the signal generated from the assay may represent only a small fraction, e.g., less than 1 part in 10,000, of the total signal generating reagent.

Thus, there remains a considerable need for improved fluidic devices, especially point-of-care devices, designed to minimize interfering optical signals.

SUMMARY OF THE INVENTION

One aspect of the invention is a fluidic device for detecting an analyte in a sample of bodily fluid. The fluidic device comprises a sample collection unit adapted to provide a sample of bodily fluid into the fluidic device, an assay assembly in fluidic communication with the sample collection unit, wherein the assay assembly is adapted to yield an optical signal indicative of the presence or quantity of the analyte in the sample of bodily fluid, and a quencher assembly in fluidic communication with said assay assembly, wherein the quencher assembly is adapted to reduce interference of the optical signal.

In some embodiments the assay assembly includes reagent chambers comprising reagents used in the assay and at least one reaction site comprising a reactant that binds the analyte. The reagents can be an enzyme conjugate and an enzyme substrate.

The quencher assembly can include quenching site in fluidic communication with the reaction site and a quenching agent at the quenching site. The quencher assembly can also include an absorbent material, which may be, for example, glass fiber, silica, paper, polyacylamide gel, agarose, or agar.

The absorbent material can be impregnated with the quenching agent. The quenching agent can be adapted to inactivate at least one reagent from the assay and thereby reduce the interfering optical signal. In some embodiments the quenching agent is 4-amino-1,11-azobenzene-3,41-disulfonic acid.

In some embodiments the assay assembly is adapted to run an immunoassay, which can be a chemiluminescent assay. The quencher assembly can be adapted to substantially eliminate the interference.

In some embodiments the fluid device has a waste chamber, wherein the waste chamber includes the quenching site.

Another aspect of the invention is a system for detecting an analyte in a sample. The system comprises a fluidic device that has an assay assembly configured to yield an optical signal that is indicative of the presence of the analyte, and a quencher assembly in fluidic communication with said assay assembly, wherein said quencher assembly is adapted to reduce interference of said optical signal, and a detection assembly for detecting said optical signal.

In some embodiments the system also includes a communication assembly for transmitting said optical signal to an external device.

In some embodiments the assay assembly comprises reagent chambers that have at least one reagent used in the assay and at least one reaction site comprising a reactant that binds the analyte. The at least one reagent can include an enzyme conjugate and an enzyme substrate.

In some embodiments the quencher assembly comprises a quenching site in fluidic communication with the reaction site and a quenching agent at the quenching site. The quencher assembly can include an absorbent material such as glass fiber, silica, paper, polyacylamide gel, agarose, or agar. The absorbent material can be impregnated with the quenching agent, which can be adapted to inactivate at least one reagent from said assay, thereby reducing said interference of said optical signal. The quenching agent can be, for example, 4-amino-1, 11-azobenzene-3,41-disulfonic acid.

In some embodiments of the system, the assay assembly is adapted to run an immunoassay, and can further be a chemiluminescent assay.

The quencher assembly can be adapted to substantially eliminate the interference.

In some embodiments of the system there is a waste chamber, wherein the waste chamber comprises the quenching site.

One aspect of the invention is a method of detecting an analyte in a sample. The method comprises allowing a sample suspected to contain the analyte to react with reagents contained in a fluidic device that has an assay assembly configured to yield an optical signal that is indicative of the presence of the analyte, and a quencher assembly in fluidic communication with said assay assembly, wherein said quencher assembly is adapted to reduce interference of said optical signal, and detecting said optical signal thereby detecting the analyte in the sample.

One aspect of the invention is a method of manufacturing a fluidic device having a quencher assembly. The method includes providing a plurality of layers of the fluidic device, affixing said layers together to provide for a fluidic network between a sample collection unit, at least one reagent chamber, at least one reaction site, and at least one quencher assembly.

In some embodiments the affixing comprising ultrasonic welding the layers together.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Fluidic Device

Figure 1:
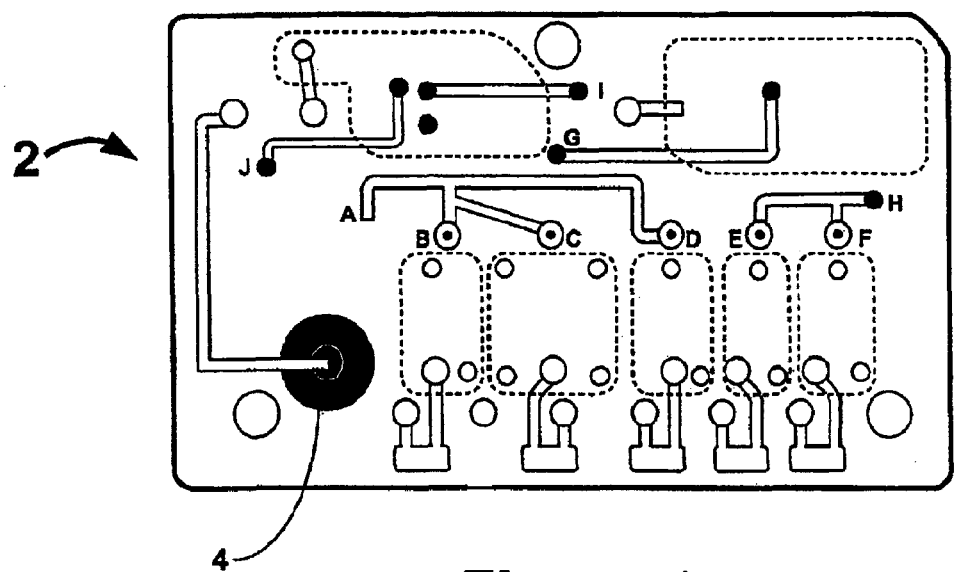
FIGS. 1 and 2 show top and bottom views of an exemplary fluidic device, illustrating the fluid connectivity.

One aspect of the invention is a fluidic device for detecting an analyte in a sample of bodily fluid. The fluidic device includes an assay assembly configured to yield an optical signal that is indicative of the presence of the analyte in the sample and a quencher assembly adapted to reduce interference of the optical signal.

The fluidic device generally has a sample collection unit, an assay assembly, fluidic channels and one or more waste chambers.

The sample collection unit comprises an inlet for receiving a sample, e.g., a bodily fluid from a subject, such as blood or urine, optionally a receptacle for holding the sample, and an outlet to a fluidic channel that connects with the assay assembly.

The assay assembly comprises (a) at least one and optionally a plurality of reagent chambers, optionally containing reagents to perform a detection assay, (b) at least one and, optionally, a plurality of reaction sites, each site comprising a surface to which is immobilized a reactant that recognizes and binds an analyte, and (3) fluidic channels that connect the reaction sites with the sample collection unit and the reagent chambers. The assay provides an optical signal indicative of the presence of an analyte of interest, which can then be detected by a detection assembly as described below. Unbound, or excess, sample and reagents remain on-board the fluidic device after the assay, and collect in a waste chamber within the fluidic device.

A reactant immobilized at a reaction site can be anything useful for detecting an analyte of interest in a sample of bodily fluid. For instance, such reactants include without limitation nucleic acid probes, antibodies, cell membrane receptors, monoclonal antibodies and polyclonal antibodies reactive with a specific analyte. Various commercially available reactants such as a host of polyclonal and monoclonal antibodies specifically developed for specific analytes can be used.

In some embodiments there are more than one reaction sites which can allow for detection of multiple analytes of interest from the same sample of bodily fluid. In some embodiments there are 2, 3, 4, 5, 6, or more reaction sites, or any other number of reaction sites as may be necessary to carry out the present invention.

In embodiments with multiple reaction sites on a fluidic device, each reaction site may be immobilized with a reactant different from a reactant on a different reaction site. In a fluidic device with, for example, three reaction sites, there may be three different reactants, each bound to a different reaction site to bind to three different analytes of interest in the sample. In some embodiments there may be different reactants bound to a single reaction site if, for example, a CCD with multiple detection areas were used as the detection device, such that multiple different analytes could be detected in a single reaction site. Exemplary reaction sites are more fully described in patent application Ser. No. 11/389,409, filed Mar. 24, 2006, which is incorporated by reference herein in its entirety.

Assay detection relies on luminescence and, in particular, chemiluminescence. In one embodiment, the assay employs an enzyme conjugate comprising, e.g., a protein conjugated with an enzyme. The enzyme can react with a substrate to generate a luminescent signal. It is contemplated that the assay can be a direct assay, a competitive assay, in which a reactant not bound to an analyte is exposed to a reagent comprising an analyte molecule conjugated to the enzyme, or as described below for detecting small molecules, the two-step assay. Another preferred assay that can be performed using the subject device is an Enzyme-Linked ImmunoSorbent Assay ("ELISA"). In another embodiment, a fluorescent dye is coupled to or used in tandem with a chemiluminescent reaction to further amplify the signal to obtain a wider range of linear response.

The assay assembly preferably comprises all of the reagents necessary to perform the assay in the fluidic device. Such reagents are on-board, or housed within the fluidic device before, during, and after the assay. In this way the only inlet for liquids from the fluidic device is preferably the bodily fluid sample initially provided to the fluidic device. There is preferably no liquid outlet in the fluidic device, however does enter and leave the fluidic device during the assay as a means of propelling liquid movement. An advantage is using such an on-board system is the easily disposable nature of the fluidic device, as well as attempting to prevent leakage from the fluidic device onto or into a detection device used to detect an optical signal produced during the assay which is indicative of the presence of an analyte of interest in the sample. Furthermore all potentially biohazardous materials are contained within the cartridge.

The reagent chambers within the assay assembly are preferably in fluidic communication with at least one reaction site, and when the fluidic device is actuated to initiate the flow of fluid as described herein, reagents contained in the reagent chambers are released into the fluidic channels.

Reagents according to the present invention include without limitation wash buffers, enzyme substrates, dilution buffers, conjugates, enzyme-labeled conjugates, DNA amplifiers, sample diluents, wash solutions, sample pre-treatment reagents including additives such as detergents, polymers, chelating agents, albumin-binding reagents, enzyme inhibitors, enzymes, anticoagulants, red-cell agglutinating agents, antibodies, or other materials necessary to run an assay on a fluidic device. An enzyme conjugate can be a conjugate with a polyclonal antibody, monoclonal antibody, hapten or other member of a binding pair (MBP) label that can yield a detectable signal upon reaction with an appropriate enzyme substrate. Non-limiting examples of such enzymes are alkaline phosphatase and horseradish peroxidase. In some embodiments the reagents comprise immunoassay reagents.

Reagent chambers can contain approximately about 50 µl to about 1 ml of fluid. In some embodiments the chamber may contain about 100 µl of fluid. The volume of liquid in a reagent chamber may vary depending on the type of assay being run or the sample of bodily fluid provided.

Liquids and other substances described herein that are transported through the fluidic device flow through channels within the fluidic device. Such channels will typically have small cross sectional dimensions. In some embodiments the dimensions are from about 0.01 mm to about 5 mm, preferably from about 0.03 mm to about 3 mm, and more preferably from about 0.05 mm to about 2 mm. Fluidic channels in the fluidic device may be created by, for example without limitation, dye cutting, machining, precision injection molding, laser etching, or any other techniques known in the art.

The fluidic device also preferably includes a quencher assembly. The quencher assembly comprises a quenching site in fluid communication with the reaction site and a quenching agent at the quenching site. The quenching assembly can optionally comprise an absorbent material impregnated with the quenching agent. In certain embodiments, the quenching site comprises or is part of the waste chamber.

The quencher assembly is typically adapted to reduce an optical signal from the fluidic device that interferes with the optical signal indicative of the presence of the analyte in the sample. In some embodiments the quencher assembly reduces the interfering optical signal by at least about 50%, at least about, 60%, at least about 70%, at least about 80%, at least about 90%, or more. In preferred embodiments the quencher assembly reduces optical interference by at least about 99%. In another preferred embodiment the quenching assembly reduces interference by at least about 99.5%. In more preferred embodiments the quencher assembly reduces optical interference by about 99.9%.

In some embodiments the quencher assembly can be adapted to physically block optical interference from the waste liquid. For example, the quencher assembly can comprise a dark coating to absorb optical interference from the fluidic device.

In some embodiments the quencher assembly can comprise an absorbent material impregnated with the quenching agent. In general, an absorbent material is a material or substance that has the power or capacity or tendency to absorb or take up liquid. Absorption mechanisms can include capillary forces, osmotic forces, solvent or chemical action, or other similar mechanisms.

An absorbent material can be a solid material, porous material, gel, porous or sintered polymer, high salt fluid, thermoplastic polymer (such as those available from Sigma, Aldrich, Porex™, etc.), polyolefin resin, or porous plastic, including, e.g., Porex™ plastics. The absorbent material may also be an aerosol particulate spray, for example, comprising porous particulate matter.

The absorbent material can be a cellulosic material such as paper, e.g., Kimwipe™, paper towel or the like.

The absorbent material can also be, for example, polyacrylamide, agarose, agar, polyethylene, polypropylene, a high molecular weight polyethylene, polyvinylidene fluoride, ethylene-vinyl acetate, polytetrafluoroethylene, stryene-acrylonitrile, polysulfone, polycarbonate, dextran, dry sephadex, polyhthalate, silica, glass fiber, or other material similar to those included herein. Additionally, an absorbent material can be any combination of the materials described herein.

In general the absorbent material is bibulous and the volume fraction of air is generally about 10-70% of the absorbent material. The absorbent material helps absorb waste liquids used in the assay and therefore prevents leakage of fluid from the fluidic device, as may be desirable to prevent contamination on or into a detection device used in conjunction with the fluidic device to detect the optical signal.

In some embodiments the absorbent material comprises at least one quenching agent which reacts with at least one reagent from said assay assembly to reduce interference of the optical signal indicative of the presence of the analyte in the sample. The quenching agent can inhibit the binding between reagents, or in preferred embodiments the quenching agent inactivates at least one and more preferably all reagents which may contribute to an interfering optical signal.

The reagent or reagents with which the quenching agent in the quencher assembly reacts to reduce the interference can be, for example without limitation, an unbound enzyme and/or an unbound substrate. The reagent with which the quenching agent reacts to reduce the interference is generally not as important as the reduction of the interference itself. The quenching agent in the quencher assembly can vary depending on the type of assay that is being performed in the fluidic device. Preferably a subject quenching agent reduces an interfering optical signal by at least about 50%, at least about 60%, at least about 70%, at least about 80%, at least about 90%, or more. In a preferred embodiment the quenching agent reduces an interfering optical signal by about 99%. In another preferred embodiments the quenching assembly reduces optical interference by at least about 99.5%. In more preferred embodiments the quenching agent reduces optical interference by at least about 99.9%.

In this way the quencher assembly can be produced with a specific assay or assays in mind and can comprise quenching agents which will satisfactorily reduce the interfering signal.

In some embodiments the quenching agent can be a chemical that is a strong non-volatile acid such as trichloroacetic acid or its salt sodium trichloracetate. The substance can also be a strong alkali such as sodium hydroxide. Other strong non-volatile acids and strong alkalis can be used in accordance with the present invention.

In some embodiments the quenching agent reduces the optical interference by inhibiting the enzyme. In an ELISA, e.g., the quenching agent can interfere with the enzyme's ability to convert the substrate to produce a luminescent signal. Exemplary enzyme inhibitors include lactose which inhibits the action of β-galactosidase on luminogenic galactosides, and phosphate salts which inhibit phosphatases.

In some embodiments the quenching agent can reduce the interference by denaturing the enzyme. By denaturing the enzyme it is unable to carry out it enzymatic function and the optical interference is suppressed or reduced. Exemplary denaturants include detergents such as sodium dodecyl sulfate (SDS), heavy metal salts such as mercuric acetate, or chelating agents such as EDTA which can sequester metal ions essential for activity of certain enzymes such as alkaline phosphatase. All types of surfactants may be used including cationic (CTMAB) and anionic (SDS).

In some embodiments the quenching agent can be a non-denaturing chemical that is incompatible with enzyme activity. Exemplary chemicals include buffers and the like that change the pH to a value where the enzyme becomes inactive and thus unable to catalyze the production of the interfering signal.

In other embodiments the quenching agent can be, for example, an organic charge-transfer molecule, including 7,7,8,8-tetracyanoquinodimethane (TCNQ), 2,3,5,6-tetrafluoro-7,7,8,8-tetracyanoquinodimethane (TFTCNQ), carbon nanotubes, mordant yellow 10 (MY) and 4-amino-1,1-azobenzene-3,4-disulfonic acid (AB). In preferred embodiments the azobenzene compounds are MY and AB, as they are considerably more water-soluble than TCNQ, TFTCNQ and carbon nanotubes. The structure of AB is shown below in:

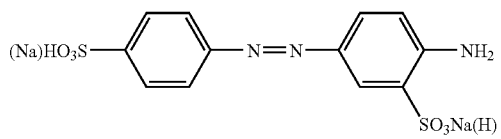

In some embodiments the quenching agent can be heavy atoms such as iodine which reduces the interference by quenching a fluorescent species used to enhance a chemiluminescent signal. In other embodiments the quenching agent can be an organic compound with an absorption spectrum overlapping the fluorescence emission spectrum of a fluorescent species used to enhance a chemiluminescent signal. In some embodiments such a quenching agent is a dark quencher such as a dispersion of carbon particles (e.g., carbon black, charcoal). Carbon can inactivate chemiluminescence by absorbing actives species, and it is also a very good quenching agent that is substantially incapable of emitting fluorescence.

In some embodiments the quenching agent can be an antioxidant, which can reduce the interference by disrupting the chemiluminescent reaction. Quenching agents that may be used in some embodiments of the invention include but are not limited to Trolox, butylated hydroxytoluene (BHT), ascorbic acid, citric acid, retinol, carotenoid terpenoids, non-carotenoid terpenoids, phenolic acids and their esters, and bioflavinoids.

In other embodiments, the quenching agent can be a singlet oxygen quencher, which can reduce the interference by disrupting the chemiluminescent reaction. Some singlet oxygen quenchers include but are not limited to 1,4 diazabicyclo[2,2,2]octane, thiol containing compounds such as methionine or cysteine, and carotenoids such as lycopene.

The substance used to impregnate or saturate the absorbent material is preferably highly concentrated, typically in large molar excess of the assay reagents.

Generally the quencher assembly possesses desirable certain properties some of which, by way of example, are now described. In embodiments in which the quencher assembly comprises an absorbent material, the absorption of waste liquids is preferably fast relative to the duration of the assay. In preferred embodiments the absorption of waste liquids occurs within a few minutes and more preferably within a few seconds.

The absorbent material preferably absorbs substantially all of the liquid waste in the fluidic device. In preferred embodiments more than 99% of the liquid in the waste chamber is absorbed. In addition to reducing the optical interference, this helps prevent liquid from leaking from the fluidic device after the assay is complete, which helps prevent contamination of a detection device as may be used with the fluidic device as described herein.

The quencher assembly's inhibition of enzyme activity should preferably be rapid, typically within a few minutes and more preferably within a few seconds.

The inhibitory enzyme reaction should be as complete as possible to ensure the interference is reduced as much as possible. In preferred embodiments the inactivation of the enzyme reaction should be more than 99% complete before the optical signal indicative of the presence of the analyte in the sample is detected by any detection mechanism that may be used with the fluidic device as described herein.

In preferred embodiments the quencher assembly comprises an absorbent material, and as such, the inactivating substance imbedded therein is preferably stable within the absorbent material. Furthermore, the quenching agent preferably dissolves within seconds to minutes of being exposed to the waste liquids.

In some embodiments the quencher assembly comprises the waste chamber. A waste chamber is generally a chamber or well in fluidic communication with the assay assembly in which assay reagents and sample which do not bind to the reaction site in the assay assembly collect after the assay. As the waste fluids remain on-board the fluidic device after the assay, the waste chamber is generally the area of the fluidic device in which any unbound or excess reagents and sample collect after the assay. In embodiments in which the quencher assembly comprises an absorbent material, the absorbent material may be adapted to be housed within the waste chamber. The absorbent material may or may not fill up the entire waste chamber, and may expand when a fluid enters the waste chamber.

The quencher assembly may also comprise a stabilizing feature adapted to stabilize or secure the absorbent material within the fluidic device. For example, a waste chamber adapted to house the absorbent material may also comprise a pin or stake projecting from the top of the waste chamber to contact and stabilize or secure the absorbent pad.

Figure 2:
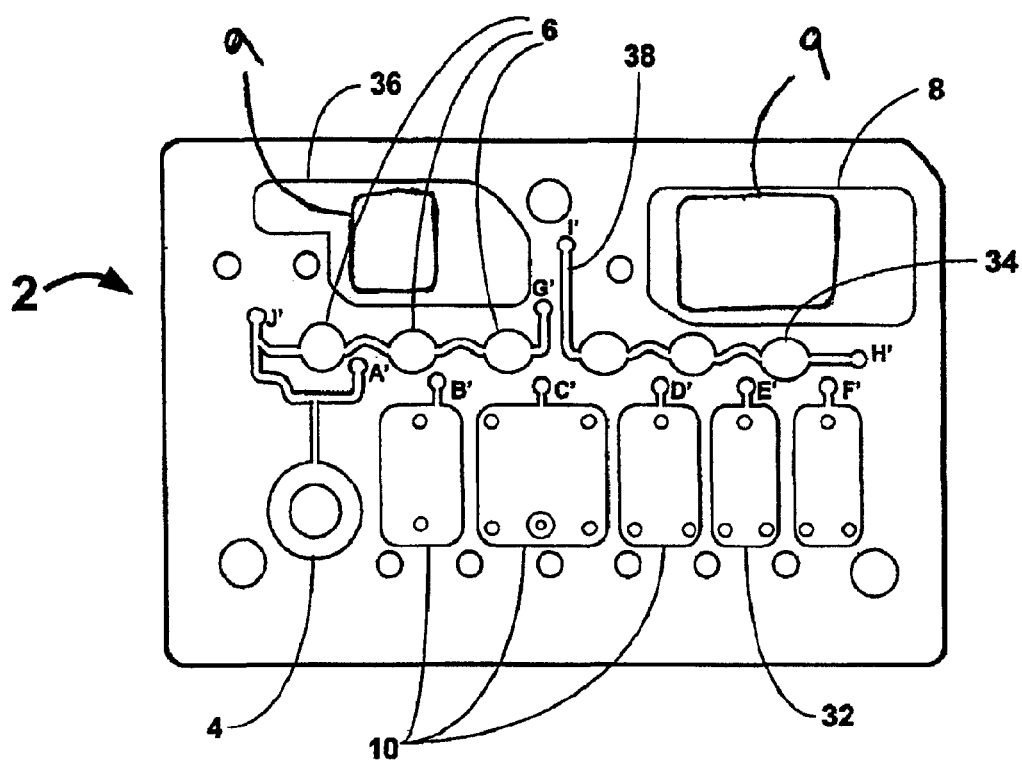

FIGS. 1 and 2 show a top and bottom view, respectively, of an exemplary fluidic device after the device has been assembled. The different layers are designed and affixed to form a three dimensional fluidic channel network. A sample collection unit 4 provides a sample of bodily fluid from a patient. As will be explained in further detail below a reader assembly comprises actuating elements (not shown) can actuate the fluidic device to start and direct the flow of a bodily fluid sample and assay reagents in the fluidic device. In some embodiments actuating elements first cause the flow of sample in the fluidic device 2 from sample collection unit 4 to reaction sites 6, move the sample upward in the fluidic device from point G' to point G, and then to waste chamber 8 in which absorbent material 9 is housed. The actuating elements then initiate the flow of reagents from reagent chambers 10 to point B', point C', and point D', then upward to points B, C, and D, respectively, then to point A, down to point A', and then to waste chamber 8 in the same manner as the sample. When the sample and the reagents enter the waste chamber 8 they encounter quencher assembly 9.

To ensure that a given photon count produced at a reaction site correlates with an accurate concentration of an analyte of interest in a sample, it is preferably advantageous to calibrate the fluidic device before detecting the photons. Calibrating a fluidic device at the point of manufacturing for example may be insufficient to ensure an accurate analyte concentration is determined because a fluidic device may be shipped prior to use and may undergo changes in temperature, for example, so that a calibration performed at manufacturing does not take into effect any subsequent changes to the structure of the fluidic device or reagents contained therein. In a preferred embodiment of the present invention, a fluidic device has a calibration assembly that mimics the assay assembly in components and design except that a sample is not introduced into the calibration assembly. Referring to FIGS. 1 and 2, a calibration assembly occupies about half of the fluidic device 2 and includes reagent chambers 32, reactions sites 34, a waste chamber 36, fluidic channels 38, and absorbent material 9. Similar to the assay assembly, the number of reagent chambers and reaction sites may vary depending on the assay being run on the fluidic device and the number of analytes being detected.

Figure 3:
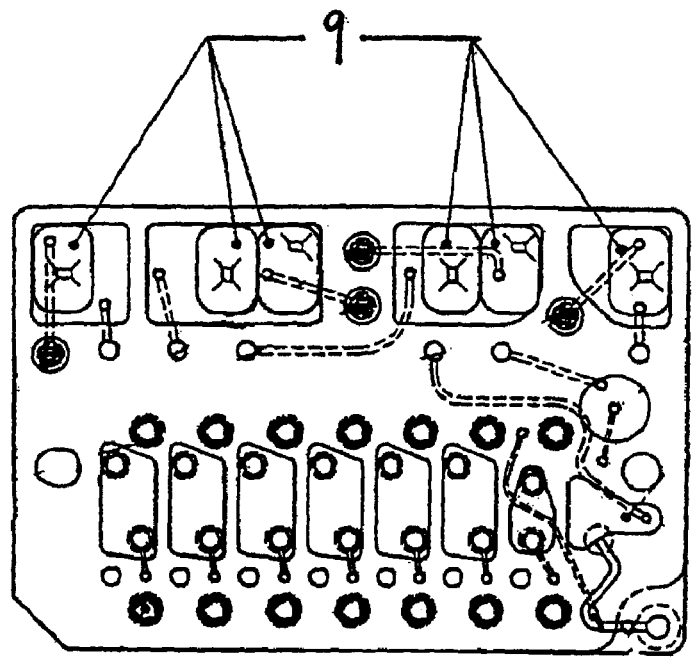
FIGS. 3 and 4 show a top and bottom view, respectively, of an exemplary fluidic of the present invention.
Figure 4:
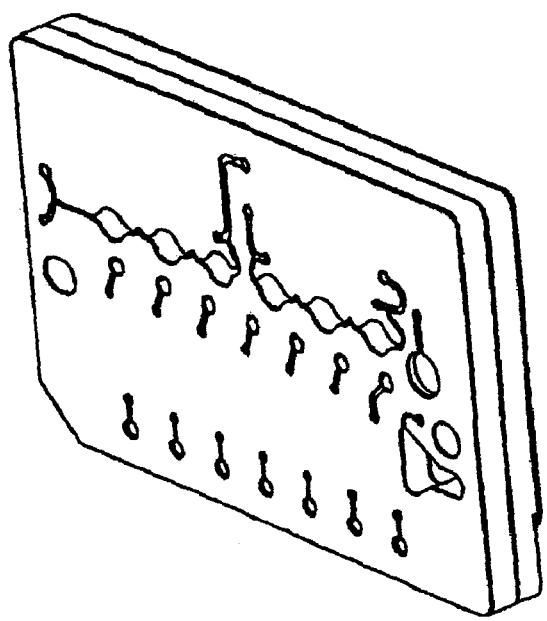

FIG. 3 is a top view of another exemplary embodiment of a fluidic device. A plurality of absorbent materials 9 are shown. FIG. 4 shows a bottom view of the embodiment from FIG. 3.

Figure 5:
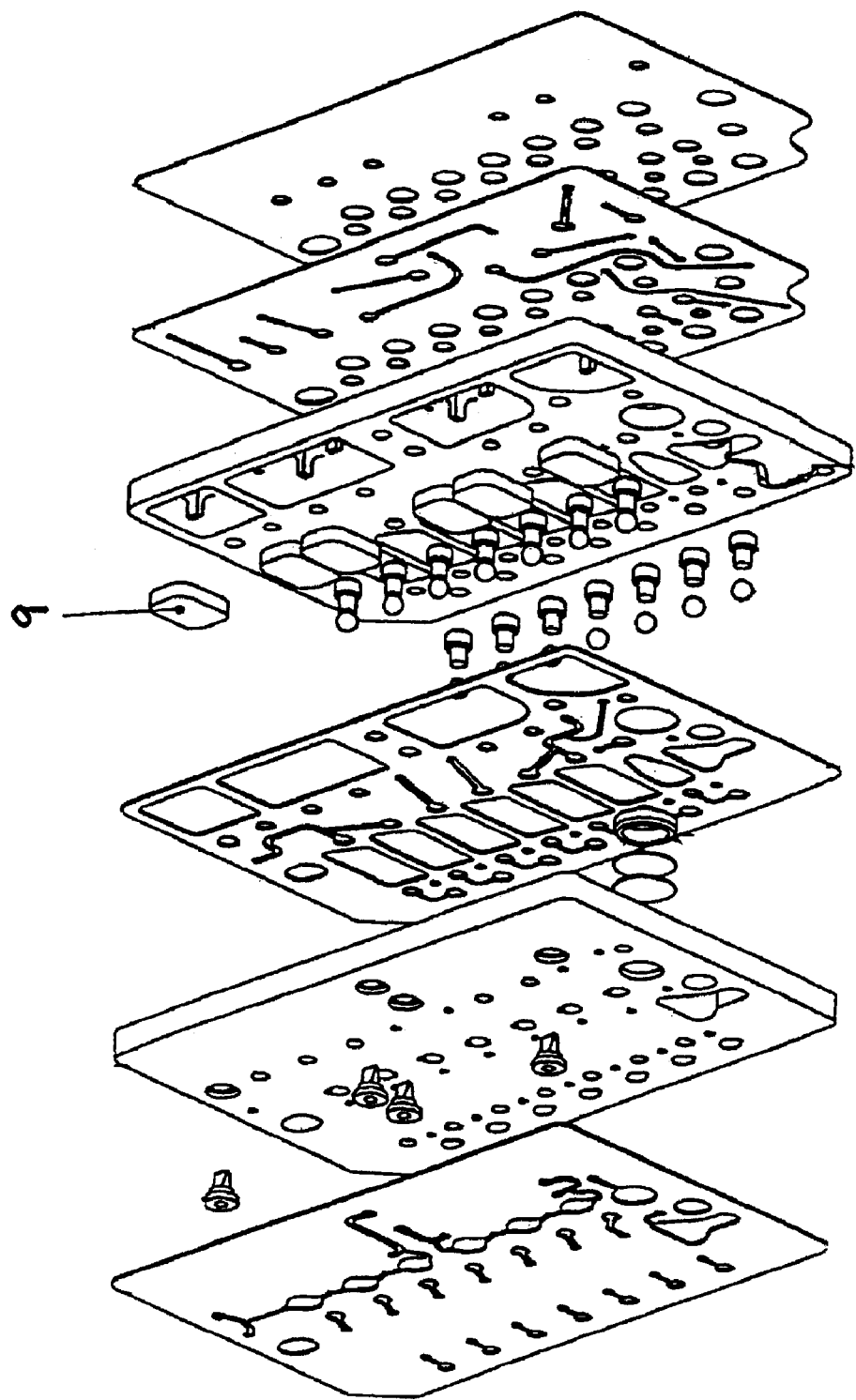
FIG. 5 illustrates the different components and layers of an exemplary fluidic device.

FIG. 5 illustrates the plurality of layers of the exemplary fluidic device shown in FIGS. 3 and 4. The position of absorbent material 9 is shown relative to the other components and layers of the fluidic device.

Figure 6:
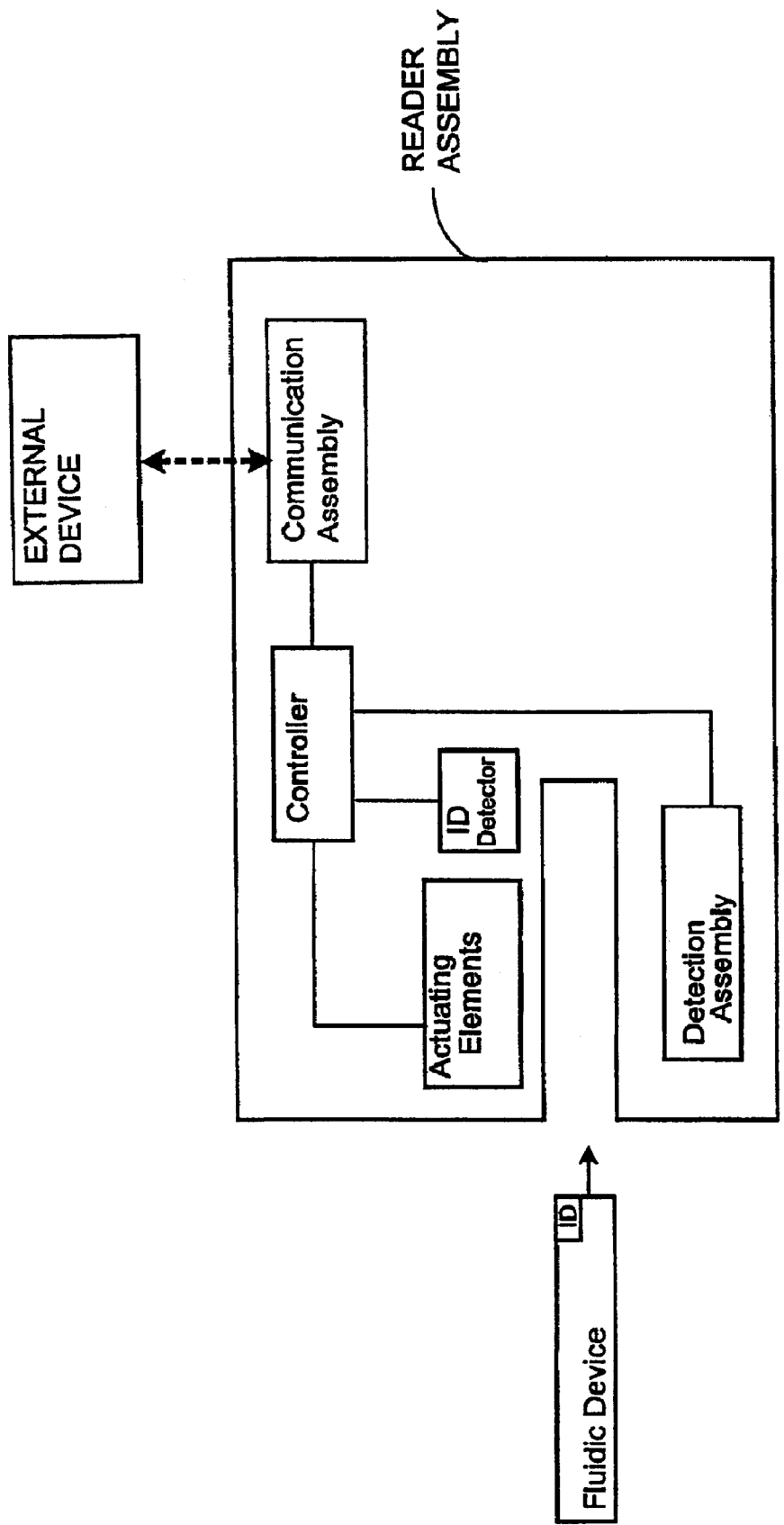
FIG. 6 shows an exemplary system of the present invention.

A detection assembly as shown in FIG. 6 then detects the optical signal indicative of the presence of the analyte in the sample, and the detected signal can then be used to determine the concentration of the analyte in the sample. FIG. 6 illustrates the position of an exemplary detection assembly that can be used to detect an optical signal from the fluidic device that is indicative of the presence of an analyte of interest in the sample. The detection assembly may be above or below the fluidic device or at a different orientation in relation to the fluidic device based on, for example, the type of assay being performed and the detection mechanism being employed.

In preferred embodiments an optical detector is used as the detection device. Non-limiting examples include a photomultiplier tube (PMT), photodiode, photon counting detector, or charge-coupled device (CCD). Some assays may generate luminescence as described herein. In some embodiments chemiluminescence is detected. In some embodiments a detection assembly could include a plurality of fiber optic cables connected as a bundle to a CCD detector or to a PMT array. The fiber optic bundle could be constructed of discrete fibers or of many small fibers fused together to form a solid bundle. Such solid bundles are commercially available and easily interfaced to CCD detectors.

Exemplary detection assemblies that may be used with the fluidic device are described in patent application Ser. No. 11/389,409, filed Mar. 24, 2006, which is incorporated by reference herein in its entirety.

Interference, or optical interference, as described herein generally means an optical signal produced in the fluidic device which interferes with the optical signal produced by bound reactants, which is indicative of the presence of an analyte of interest. Typically, such an interfering signal is produced in the waste chamber where the reagents which do not bind to the reaction sites accumulate and encounter one another. The accumulation of waste liquids can produce such interference when, for example, an enzyme used in an assay to increase assay sensitivity reacts with an unbound substrate, creating an optical signal that interferes with the optical signal generated by bound reactants.

Method of Use

Another aspect of the invention is a method of detecting an analyte in a sample. The method comprises allowing a bodily fluid sample suspected to contain the analyte to react with reactants contained in a fluidic device which has an assay assembly configured to yield an optical signal that is indicative of the presence of the analyte and a quencher assembly adapted to reduce interference of said optical signal, and detecting the optical signal thereby detecting the analyte in the sample.

Any sample of bodily fluids suspected to contain an analyte of interest can be used in conjunction with the subject system or devices. Commonly employed bodily fluids include but are not limited to blood, serum, saliva, urine, gastric and digestive fluid, tears, stool, semen, vaginal fluid, interstitial fluids derived from tumorous tissue, and cerebrospinal fluid. In some embodiments, the bodily fluids are provided directly to the fluidic device without further processing. In some embodiments, however, the bodily fluids can be pre-treated before performing the analysis with the subject fluidic devices. The choice of pre-treatments will depend on the type of bodily fluid used and/or the nature of the analyte under investigation. For instance, where the analyte is present at low level in a sample of bodily fluid, the sample can be concentrated via any conventional means to enrich the analyte. Where the analyte is a nucleic acid, it can be extracted using various lytic enzymes or chemical solutions according to the procedures set forth in Sambrook et al. ("Molecular Cloning: A Laboratory Manual"), or using nucleic acid binding resins following the accompanying instructions provided by manufactures. Where the analyte is a molecule present on or within a cell, extraction can be performed using lysing agents including but not limited to denaturing detergent such as SDS or non-denaturing detergent such as Thesit®, sodium deoxylate, triton X-100, and tween-20.

A bodily fluid may be drawn from a patient and brought into the fluidic device in a variety of ways, including but not limited to, lancing, injection, or pipetting. In some embodiments, a lancet punctures the skin and draws the sample into the fluidic device using, for example, gravity, capillary action, aspiration, or vacuum force. In another embodiment where no active mechanism is required, a patient can simply provide a bodily fluid to the fluidic device, as for example, could occur with a blood or saliva sample. The collected fluid can be placed in the sample collection unit within the fluidic device where the fluidic device can automatically detect the required volume of sample to be used in the assay. In yet another embodiment, the fluidic device comprises at least one microneedle which punctures the skin. The microneedle can be used with a fluidic device alone, or can puncture the skin after the fluidic device is inserted into a reader assembly.

Sample collections techniques which may be used herein are described in patent application Ser. No. 11/389,409, filed Mar. 24, 2006, which is incorporated by reference herein in its entirety.

In some embodiments a sample of bodily fluid can first be provided to the fluidic device by any of the methods described herein. The fluidic device can then be inserted into a reader assembly as shown in FIG. 6. An identification detector housed within the reader assembly can detect an identifier of the fluidic device and communicate the identifier to a communication assembly, which is preferably housed within the reader assembly. The communication assembly then transmits the identifier to an external device which transmits a protocol to run on the fluidic device based on the identifier to the communication assembly. A controller preferably housed within the reader assembly controls actuating elements including at least one pump and one valve which interact with the fluidic device to control and direct fluid movement within the device. The reader assembly and its components illustrated in FIG. 6 are more fully described in patent application Ser. No. 11/389,409, filed Mar. 24, 2006, which is incorporated by reference herein in its entirety.

The fluidic device is preferably initially calibrated using a calibration assembly by running the same reagents as will be used in the assay through the calibration reaction sites, and then an optical signal from the reactions sites is detected by the detection means, and the signal is used in calibrating the fluidic device. Calibration techniques that may be used in the fluidic device herein can be found in patent application Ser. No. 11/389,409, filed Mar. 24, 2006, which is incorporated by reference herein in its entirety. The sample containing an analyte is introduced into the fluidic channel. The sample may be diluted, mixed, and/or and further separated into plasma or other desired component using a filter. The sample then flows through the reaction sites and analytes present therein will bind to reactants bound thereon. The sample fluid is then flushed out of the reaction wells into a waste chamber. Depending on the assay being run, appropriate reagents are directed through the reaction sites via the channels to carry out the assay. Any wash buffers and other reagents used in the various steps, including the calibration step, are collected in at least one waste chamber. The signal produced in the reaction sites is then detected by any of the detection methods described herein.

A variety of assays may be performed in a fluidic device according to the present invention to detect an analyte of interest in a sample.

The detection assay relies on luminescence and, in particular, chemiluminescence. In one embodiment, the assay employs an enzyme conjugate comprising, e.g., a protein conjugated with an enzyme. The enzyme can react with a substrate to generate a luminescent signal. It is contemplated that the assay can be a direct assay or a competitive assay, in which a reactant not bound to an analyte is exposed to a reagent comprising an analyte molecule conjugated to the enzyme. Further, a fluorescent compound may be used in tandem or coupled with the chemiluminescent reaction, in order to linearly multiply the signal output of the reaction.

Figure 7:
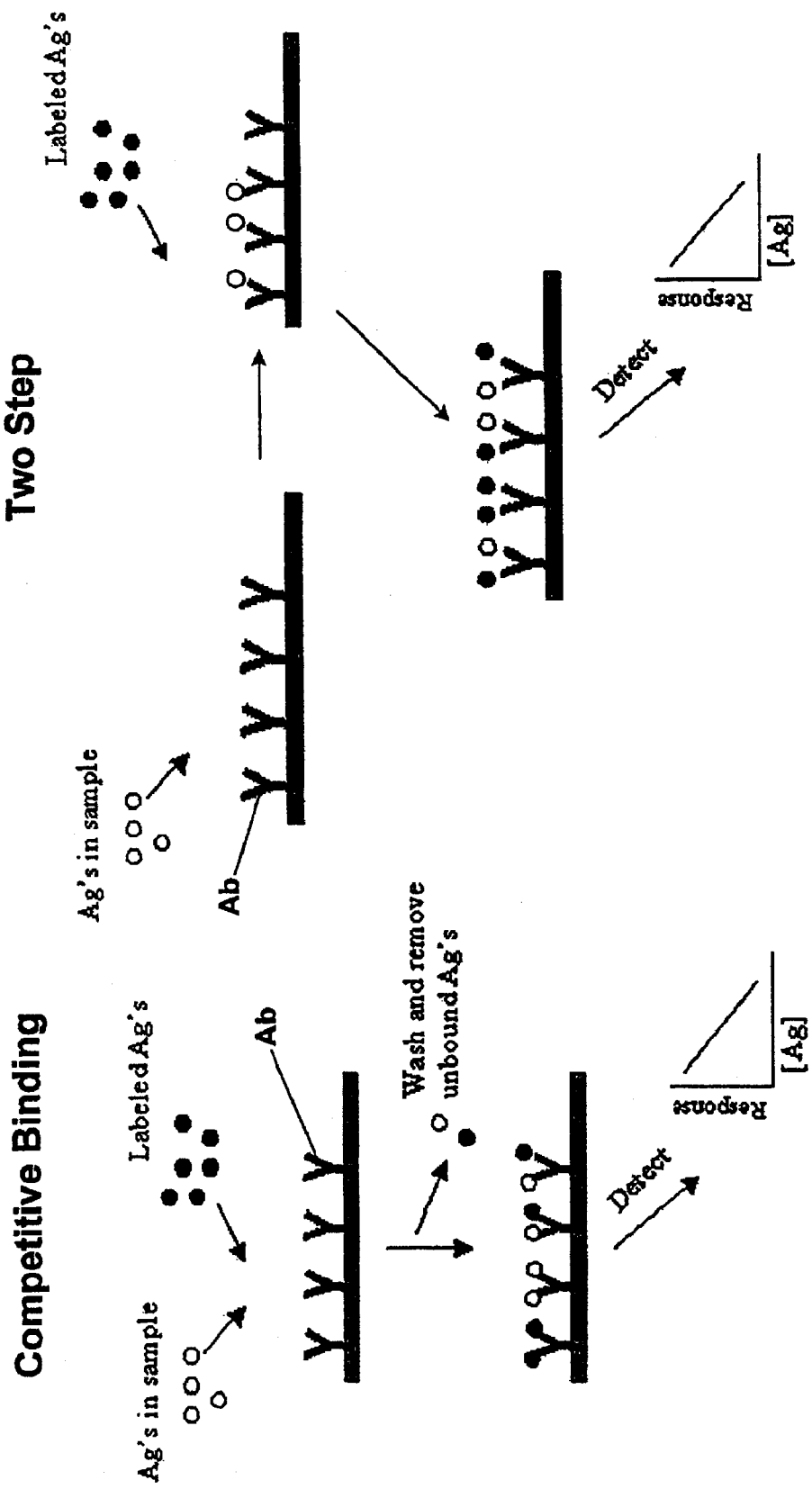
FIG. 7 shows a two-step assay.

In an exemplary two-step assay shown in FIG. 7, the sample containing analyte ("Ag") first flows over a reaction site containing antibodies ("Ab"). The antibodies bind the analyte present in the sample. After the sample passes over the surface, a solution with analyte conjugated to a marker ("labeled Ag") at a high concentration is passed over the surface. The conjugate saturates any of the antibodies that have not yet bound the analyte. Before equilibrium is reached and any displacement of pre-bound unlabelled analyte occurs, the high-concentration conjugate solution is washed off. The amount of conjugate bound to the surface is then measured by the appropriate technique, and the detected conjugate is inversely proportional to the amount of analyte present in the sample.

Figure 8:
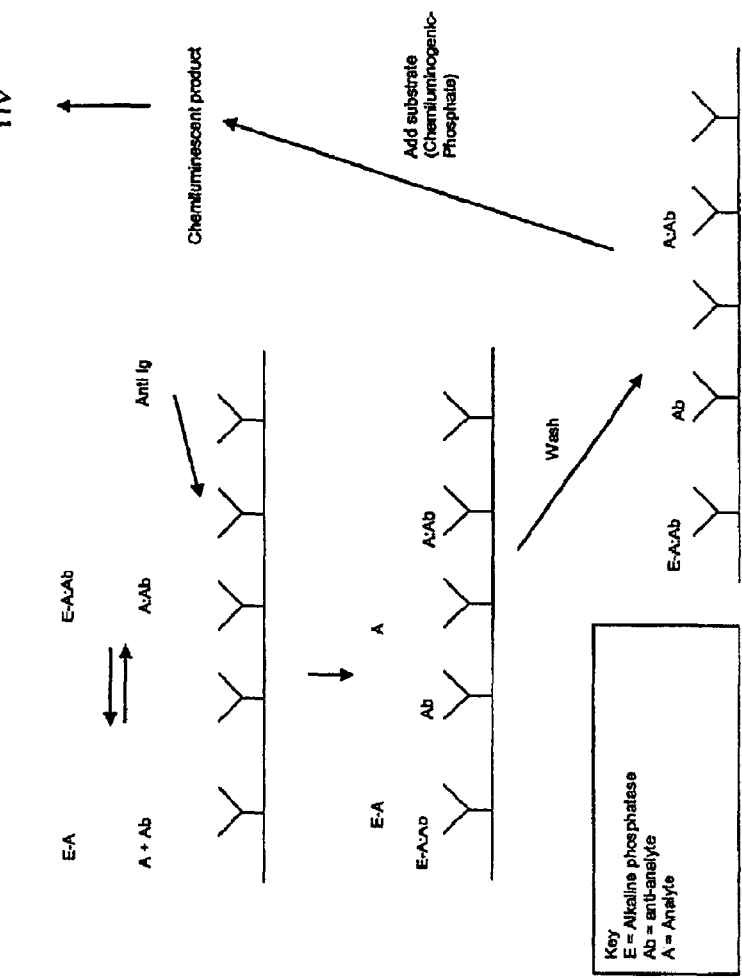
FIG. 8 depicts an exemplary chemiluminescent assay.

An exemplary measuring technique for a two-step assay is a chemiluminescence enzyme immunoassay as shown in FIG. 8. As is known in the field, the marker can be a commercially available marker such as a dioxetane-phosphate, which is not luminescent but becomes luminescent after hydrolysis by, for example, alkaline phosphatase. An enzyme such as alkaline phosphatase is exposed to the conjugate to cause the substrate to luminesce. In some embodiments the substrate solution is supplemented with enhancing agents such as, without limitation, fluorescein in mixed micelles, soluble polymers, or PVC which create a much brighter signal than the luminophore alone. The mechanism by which the quencher assembly functions to reduce interference is not critical to the functionality of the present invention, as long as the interference is reduced by a sufficient amount.

An ELISA is another exemplary assay for which an optical quencher can be used to remove an interfering signal generated by reactants to a reaction site. In a typical ELISA, a sample containing an antigen of interest is passed over the reaction site, to which analytes of interest in the sample will bind by virtue of antibody molecules (directed to the antigen) adsorbed to the reaction site. Then, enzyme-labeled antibody conjugate (directed to the antigen and selected such that the antibody bound to the reaction site does not block binding of the conjugate) is passed over the reaction site, allowed to bind, then displaced by the substrate. Enzyme causes the substrate to produce an optical signal. Unbound reagents which end up in the waste chamber can similarly produce interfering signals.

In some embodiments the label is coupled directly or indirectly to a molecule to be detected such as a product, substrate, or enzyme, according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule is covalently bound to a polymer. The ligand then binds to an anti-ligand molecule which is either inherently detectable or covalently bound to a signal system, such as a detectable enzyme, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody.

In some embodiments the label can also be conjugated directly to signal generating compounds, for example, by conjugation with an enzyme. Enzymes of interest as labels will primarily be hydrolases, particularly phosphatases, esterases and glycosidases, or oxidoreductases, particularly peroxidases. Chemiluminescent compounds include luciferin, and 2,3-dihydrophthalazinediones, such as luminol, dioxetanes and acridinium esters.

Methods of detecting labels are well known to those of skill in the art. Detection can be accomplished using of electronic detectors such as digital cameras, charge coupled devices (CCDs) or photomultipliers and phototubes, or other detection devices. Similarly, enzymatic labels are detected by providing appropriate substrates for the enzyme and detecting the resulting reaction product. Finally, simple colorimetric labels are often detected simply by observing the color associated with the label. For example, conjugated gold often appears pink, while various conjugated beads appear the color of the bead.

Suitable chemiluminescent sources include a compound which becomes electronically excited by a chemical reaction and may then emit light which serves as the detectible signal. A diverse number of families of compounds have been found to provide chemiluminescence under a variety or conditions. One family of compounds is 2,3-dihydro-1,4-phthalazinedione. A frequently used compound is luminol, which is a 5-amino compound. Other members of the family include the 5-amino-6,7,8-trimethoxy- and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, for example, p-nitrophenyl and a peroxide such as hydrogen peroxide, under basic conditions. Other useful chemiluminescent compounds that are also known include —N-alkyl acridinum esters and dioxetanes. Alternatively, luciferins may be used in conjunction with luciferase or lucigenins to provide bioluminescence.

In some embodiments immunoassays are run on the fluidic device. While competitive binding assays, which are well known in the art, may be run in some embodiments, in some embodiments a two-step method is used which eliminates the need to mix a conjugate and a sample before exposing the mixture to an antibody, which may be desirable when very small volumes of sample and conjugate are used, as in the fluidic device of the present invention. A two-step assay has additional advantages over the competitive binding assays when use with a fluidic device as described herein. It combines the ease of use and high sensitivity of a sandwich (competitive binding) immunoassay with the ability to assay small molecules.

An exemplary two-step assay shown in FIG. 8 has been described herein, as has an exemplary measuring technique for the two-step assay—a chemiluminescence enzyme immunoassay as shown in FIG. 8.

The term "analytes" according to the present invention includes without limitation drugs, prodrugs, pharmaceutical agents, drug metabolites, biomarkers such as expressed proteins and cell markers, antibodies, serum proteins, cholesterol, polysaccharides, nucleic acids, biological analytes, biomarkers, genes, protein, or hormones, or any combination thereof. At a molecular level, the analytes can be polypeptide, proteins, glycoprotein, polysaccharide, lipid, nucleic acid, and combinations thereof.

A more complete list of analytes which can be detected using a fluidic device and methods described herein are included in patent application Ser. No. 11/389,409, filed Mar. 24, 2006, which is incorporated by reference herein in its entirety.

One aspect of the invention is a method of manufacturing a fluidic device having a quencher assembly. The method comprises providing a plurality of layers of the fluidic device, and affixing the layers to provide for a fluidic network between a sample collection unit, at least one reagent chamber, at least one reaction site, and at least one waste chamber comprising an quencher assembly.

In some embodiments at least one of the different layers of the fluidic device may be constructed of polymeric substrates. Non limiting examples of polymeric materials include polystyrene, polycarbonate, polypropylene, polydimethylsiloxanes (PDMS), polyurethane, polyvinylchloride (PVC), polymethylmethacrylate and polysulfone.

Manufacturing of the fluidic channels may generally be carried out by any number of microfabrication techniques that are well known in the art. For example, lithographic techniques are optionally employed in fabricating, for example, glass, quartz or silicon substrates, using methods well known in the semiconductor manufacturing industries such as photolithographic etching, plasma etching or wet chemical etching. Alternatively, micromachining methods such as laser drilling, micromilling and the like are optionally employed. Similarly, for polymeric substrates, well known manufacturing techniques may also be used. These techniques include injection molding. Stamp molding and embossing methods where large numbers of substrates are optionally produced using, for example, rolling stamps to produce large sheets of microscale substrates or polymer microcasting techniques where the substrate is polymerized within a micromachined mold. Dye casting may also be used.

In preferred embodiments the different layers of the fluidic device are ultrasonically welded together according to methods known in the art. The layers may also be coupled together using other methods, including without limitation, stamping, thermal bonding, adhesives or, in the case of certain substrates, e.g., glass, or semi-rigid and non-rigid polymeric substrates, a natural adhesion between the two components.

FIG. 5 shows an embodiment of the invention in which a fluidic device 2 is comprised of a plurality of different layers of material. Features as shown are, for example, cut in the polymeric substrate such that when the layers are properly positioned when assembly will form a fluidic network. In some embodiments more or fewer layers may be used to construct a fluidic device to carry out the purpose of the invention.

The quencher assembly has been described herein and in some embodiments can comprise an absorbent material. In such embodiments the quencher assembly can be produced by applying the quenching agent into the absorbent material. This can be accomplished by any number of techniques well known in the art, such as pipetting the liquid onto the absorbent material until the absorbent material is substantially imbedded in the absorbent material, or simply allowing the absorbent material to absorb the quenching agent. The amount of saturation of the absorbent material may vary, as long as a sufficient amount of the quenching agent is incorporated into the absorbent material to produce an inhibitory effect on at least assay reagent.

After the quenching agent is added to the absorbent material, the absorbent material is then dried. The drying step can be accomplished by any suitable technique such as freeze drying, drying under flowing gas with temperature elevation, or simply passive drying by allowing water in the absorbent material to evaporate.

Once dry, the absorbent material incorporating the quenching agent can then be placed into a fluidic device as described during the manufacturing process where it can be used to reduce optical interference in an assay performed within the fluidic device. The placement inside the fluidic device can be by any known technique and can simply be manually placing it into the fluidic device. As described above, the absorbent material is preferably placed in a waste chamber adapted to collect unbound liquids used inside the fluidic device.

Example

A 1×0.5 inch piece of Whatman #32 glass fiber mat (item 10 372 968) was impregnated with 50 uL of 15% w/v 4-amino-1,1-azobenzene-3,4-disulfonic acid (0.4 M) in water then dried in a "dry box".

In assays using alkaline-phosphatase (from bovine intestine)-labeled reagents (APase coupled to haptens or to antibodies at concentrations of up to about 10 ug/mL in a dilute tris buffer) and either Lumigen's Lumiphos™ 530, or KPL Phosphoglow™ AP substrates (both are dioxetanes and have an esterified phosphate residue on which the enzyme acts) used as supplied by the vendors (100 uM in dioxetane), the result was about 200 uL of enzyme and 200 uL of substrate in the waste chamber, thus exposed to the adsorbent material.

After an initial glow rate of 38,550 counts/second (observed by placing the fluidic device in a Molecular Devices M5 luminometer such that the waste chamber was being interrogated), the intensity dropped to about 100 counts/second within a few seconds after adding the adsorbent material (the noise level of the luminometer was about 100 counts/second). In other words, more than 99% of the optical interference was eliminated.

The azobenzene acted in an inhibitory manner on both the enzyme and the substrate. The enzyme was inactivated by the acidity of the reagent, and likely by other mechanisms as well. The substrate was chemically modified by the azobenzene such that it is no longer a substrate for alkaline phosphatase.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of detecting an analyte in a sample, comprising:
   (a) allowing a sample suspected to contain the analyte to react with at least one reactant contained in a fluidic device, said device comprising:
      (i) an assay assembly configured to yield an optical signal that is indicative of the presence of the analyte, said assay assembly comprising:
         (1) a reagent chamber comprising at least one reagent used in said assay; and
         (2) at least one reaction site comprising a reactant that binds said analyte,
            wherein said assay assembly is adapted to yield an optical signal indicative of the presence of the analyte in the sample, and
            wherein the at least one reagent reacts with a second reagent in said assay assembly to produce the optical signal; and
      (ii) a quencher assembly in fluidic communication with but in a separate location from said assay assembly, wherein said quencher assembly comprises a quenching agent that inhibits an enzymatic reaction between the at least one reagent and the second reagent in said quencher assembly to reduce signals that interfere with the optical signals detected from said assay assembly; and
   (b) channeling unreacted reactants to said quencher assembly where interfering signals from said unreacted reactants are quenched with said quenching agent; and
   (c) detecting said optical signal thereby detecting the analyte in the sample.

2. The method of claim 1, wherein said at least one reagent comprises an enzyme conjugate or an enzyme substrate.

3. The method of claim 1, wherein said quenching agent is contained in a quenching site of the quencher assembly.

4. The method of claim 3, wherein said quencher assembly further comprises an absorbent material.

5. The method of claim 4, wherein said absorbent material is impregnated with said quenching agent.

6. The method of claim 4, wherein said absorbent material is selected from the group consisting of glass fiber, silica, paper, polyacylamide gel, agarose, and agar.

7. The method of claim 4, wherein said quenching agent is a denaturing agent.

8. The method of claim 7, wherein said quenching agent is 4-amino-1,11-azobenzene-3,41-disulfonic acid.

9. The method of claim 1, wherein said assay assembly is adapted to run a chemiluminescent assay.

10. The method of claim 1, wherein said quencher assembly is adapted to substantially eliminate optical interference from unreacted reagent.

11. The method of claim 3, further comprising a waste chamber, wherein said waste chamber comprises said quenching site.

12. The method of claim 1, wherein said sample of bodily fluid is blood.

13. The method of claim 1, wherein the optical signal is a luminescent signal.

14. The method of claim 13, wherein the luminescent signal is a chemiluminescent signal.

15. A method of detecting an analyte in a sample, comprising:
   (a) allowing a sample suspected to contain the analyte to react with at least one reactant contained in a fluidic device, said device comprising:
      (i) an assay assembly comprising at least one reaction site, said reaction site comprising a surface and immobilized thereon a reactant that forms a complex comprising the analyte;
      (ii) a first reagent chamber comprising an enzyme conjugate;
      (iii) a second reagent chamber comprising an enzyme substrate, wherein the enzyme substrate reacts with the enzyme conjugate to produce a chemiluminescent signal;
      (iv) fluidic channels that connect the reagent chambers with the at least one reaction site;
      (v) a quencher assembly at a separate location from the assay assembly, the quencher assembly comprising an absorbent material and a quenching agent, wherein the quenching agent inhibits the chemiluminescent reaction between the enzyme conjugate and the enzyme substrate to reduce signals that interfere with the chemiluminescent signal detected from said assay assembly; and
      (vi) a plurality of fluidic channels that connect the sample collection unit and the quencher assembly with the assay assembly
   (b) channeling unreacted reactants to said quencher assembly where interfering signals from said unreacted reactants are quenched with said quenching agent;
   (c) detecting said chemiluminescent signal thereby detecting the analyte in the sample.

16. The method of claim 15, wherein said quencher assembly further comprises a waste chamber connected through a fluid channel with the assay assembly, wherein the waste chamber comprises the absorbent material.

17. The method of claim 15, wherein said absorbent material is selected from the group consisting of glass fiber, silica, paper, polyacylamide gel, agarose, or agar.

18. The method of claim 17, wherein said quenching agent is 4-amino-1,11-azobenzene-3,41-disulfonic acid and said enzyme conjugate is an alkaline phosphatase-labeled reagent.

19. The method of claim 15, wherein said assay assembly is adapted to run an immunoassay.

* * * * *